(12) United States Patent
Hofstadt et al.

(10) Patent No.: US 7,850,842 B2
(45) Date of Patent: Dec. 14, 2010

(54) ZR02-BASE CATALYST CARRIER AND METHOD FOR THE PRODUCTION THEREOF

(75) Inventors: Otto Hofstadt, Speyer (DE); Michael Hesse, Worms (DE); Götz-Peter Schindler, Mannheim (DE); Klaus Harth, Altleiningen (DE); Falk Simon, Bürstadt-Riedrode (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1115 days.

(21) Appl. No.: 10/513,041

(22) PCT Filed: May 2, 2003

(86) PCT No.: PCT/EP03/04625

§ 371 (c)(1),
(2), (4) Date: Nov. 1, 2004

(87) PCT Pub. No.: WO03/092887

PCT Pub. Date: Nov. 13, 2003

(65) Prior Publication Data

US 2006/0046929 A1    Mar. 2, 2006

(30) Foreign Application Priority Data

May 3, 2002    (DE) .................. 102 19 879

(51) Int. Cl.
*C10G 35/06* (2006.01)
*B01J 23/00* (2006.01)
*B01J 21/00* (2006.01)
*B01J 20/00* (2006.01)

(52) U.S. Cl. .............. 208/137; 208/133; 208/134; 208/135; 208/136; 208/138; 502/104; 502/115; 502/116; 502/118; 502/150; 502/242; 502/258; 502/349; 502/439

(58) Field of Classification Search .......... 502/240, 502/258, 349, 305–323, 325–339, 439, 104, 502/115, 116, 118, 150, 242; 208/133–138
See application file for complete search history.

(56) References Cited

U.S. PATENT DOCUMENTS

| | | | | |
|---|---|---|---|---|
| 3,159,569 | A * | 12/1964 | Hansford | 208/110 |
| 4,631,267 | A | 12/1986 | Lachmann et al. | |
| 5,030,601 | A * | 7/1991 | Michel et al. | 501/103 |
| 5,032,556 | A * | 7/1991 | Mori et al. | 501/106 |
| 5,104,832 | A * | 4/1992 | Michel et al. | 501/103 |
| 5,525,560 | A * | 6/1996 | Yamazaki et al. | 501/103 |
| 5,728,636 | A * | 3/1998 | Nawa et al. | 501/105 |
| 5,863,850 | A * | 1/1999 | Nawa et al. | 501/105 |
| 5,968,652 | A * | 10/1999 | Hanggi et al. | 428/405 |
| 6,391,276 | B1 * | 5/2002 | Suda et al. | 423/598 |
| 6,432,861 | B1 * | 8/2002 | Breitscheidel et al. | 502/103 |
| 6,576,804 | B1 | 6/2003 | Heineke et al. | |
| 6,992,040 | B2 * | 1/2006 | Muller et al. | 502/327 |
| 2002/0004544 | A1 * | 1/2002 | Kolb et al. | 524/413 |
| 2003/0163012 | A1 | 8/2003 | Heineke et al. | |

FOREIGN PATENT DOCUMENTS

| | | |
|---|---|---|
| DE | 196 54 391 | 7/1998 |
| EP | 0 700 718 | 3/1996 |
| EP | 0 716 883 | 6/1996 |
| EP | 1 074 301 | 2/2001 |
| FR | 2 590 887 | 6/1987 |
| GB | 1 356 249 | 6/1974 |
| WO | WO 02/051547 | 7/2002 |

OTHER PUBLICATIONS 96-279392/29—Badi Dec. 17, 1994, Irgang et al. (Jun. 1996).

* cited by examiner

*Primary Examiner*—Cam N Nguyen
(74) *Attorney, Agent, or Firm*—Novak Druce + Quigg LLP

(57) ABSTRACT

The invention relates to a process for preparing a catalyst support, in which zirconium dioxide powder is mixed with a binder, if desired a pore former, if desired an acid, water and, if desired, further additives to give a kneadable composition and the composition is homogenized, shaped to produce shaped bodies, dried and calcined, wherein the binder is a monomeric, oligomeric or polymeric organosilicon compound. Suitable binders are monomeric, oligomeric or polymeric silanes, alkoxysilanes, aryloxysilanes, acryloxysilanes, oximinosilanes, halosilanes, aminoxysilanes, aminosilanes, amidosilanes, silazanes or silicones. The invention also provides the catalyst support which has been prepared in this way, a catalyst comprising the support and its use as dehydrogenation catalyst.

6 Claims, No Drawings

ZRO2-BASE CATALYST CARRIER AND METHOD FOR THE PRODUCTION THEREOF

The invention relates to a catalyst support, to a process for its preparation, to a dehydrogenation catalyst comprising the support and to the use of the dehydrogenation catalyst.

It is known that zirconium dioxide can be used as catalyst support for dehydrogenation catalysts.

EP-A 0 716 883 discloses a catalyst support consisting essentially of monoclinic zirconium dioxide. This is prepared by addition of a zirconyl nitrate or zirconyl chloride solution to an aqueous ammonia solution, which results in the pH dropping from 14 to 6, washing the precipitated product, drying, calcination and tableting. The catalyst support produced in this way comprises from 85 to 100% by weight of monoclinic zirconium dioxide.

DE-A 196 54 391 describes the preparation of a dehydrogenation catalyst by impregnation of essentially monoclinic $ZrO_2$ with a solution of $Pt(NO_3)_2$ and $Sn(OAc)_2$ or by impregnation of the $ZrO_2$ with a first solution of $Cr(NO_3)_3$ and subsequently a second solution of $La(NO_3)_3$. The impregnated supports are dried and subsequently calcined. The catalysts obtained in this way are used as dehydrogenation catalyst for the dehydrogenation of propane to propene.

The catalysts of the prior art are still capable of improvement in respect of their activity and their operating life.

It is an object of the present invention to provide a catalyst support for the production of dehydrogenation catalysts having improved properties, in particular an improved catalyst activity, and the corresponding dehydrogenation catalysts themselves.

We have found that this object is achieved by a process for preparing a catalyst support, in which zirconium dioxide powder is mixed with a binder, if desired a pore former, if desired an acid, water and, if desired, further additives to give a kneadable composition and the composition is homogenized, shaped to produce shaped bodies, dried and calcined, wherein the binder is a monomeric, oligomeric or polymeric organosilicon compound.

The object is also achieved by, in particular, the catalyst support obtainable by this process.

According to the present invention, it has been found that mixing essentially monoclinic zirconium dioxide powder which has a high surface area with an organosilicon compound which forms $SiO_2$ on calcination as binder, shaping the mixture to produce shaped bodies such as pellets, extrudates and spheres and calcining the shaped bodies enables catalyst supports having a high mechanical stability and a pore structure which is very well suited to the dehydrogenation of alkanes to be prepared. The catalyst supports of the present invention have sufficient stability to withstand several hundred oxidative regeneration cycles without mechanical damage and a drop in activity.

The organosilicon compounds used as binder are generally liquid. As a result, the high surface area zirconium dioxide is uniformly wetted with the organosilicon compound on mixing, so that the zirconium dioxide particles are enclosed and partially impregnated by the organosilicon compound. This results in a high bond strength between the zirconium dioxide particles and a very good mechanical stability of the shaped catalyst support bodies obtained. On calcination of the shaped catalyst support bodies, the organic radicals of the organosilicon binder are burnt. This forms $SiO_2$ which is very finely dispersed in the zirconium dioxide matrix. The combustion of the organic radicals of the organosilicon binder forms additional pores. Due to the uniform distribution of the organosilicon binder in the zirconium dioxide matrix, these pores are likewise very uniformly distributed. As a result, the total porosity of the catalyst support is increased. In addition, the presence of $SiO_2$ stabilizes the zirconium dioxide against thermal sintering. This becomes increasingly pronounced, the more uniformly the silicon dioxide is distributed.

Compounds suitable as organosilicon binder are monomeric, oligomeric or polymeric silanes, alkoxysilanes, aryloxysilanes, acyloxysilanes, oximinosilanes, halosilanes, aminoxysilanes, aminosilanes, amidosilanes, silazanes and silicones, as are described, for example, in Ullmann's Encyclopedia of Industrial Chemistry, Vol. A24, on pages 21 to 56. These include, in particular, the monomeric compounds of the formulae (I) to (VI):

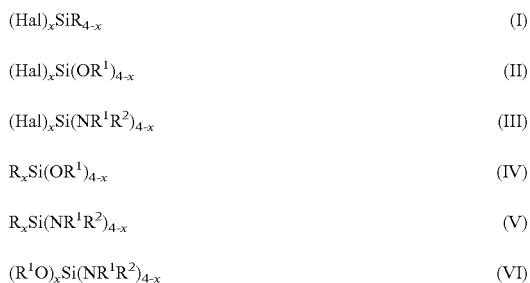

where

Hal are each, independently of one another, halogen (F, Cl, Br or I),

R are each, independently of one another, H or a substituted or unsubstituted alkyl, alkenyl, alkynyl, cycloalkyl, cycloalkenyl, arylalkyl or aryl radical, $R^1$, $R^2$ are each, independently of one another, H or a substituted or unsubstituted alkyl, acyl, arylalkyl or aryl radical, and x is from 0 to 4.

R, $R^1$ and $R^2$ can each be H or an alkyl radical, preferably a $C_1$-$C_6$-alkyl radical, which may be linear or branched. If R is an alkyl radical, R is particularly preferably methyl, ethyl, n-propyl, isopropyl, n-butyl, sec-butyl or tert-butyl, especially methyl or ethyl. R, $R^1$ and $R^2$ can also be an aryl radical, preferably phenyl, or an arylalkyl radical, preferably benzyl.

R can also be an alkenyl radical, preferably a $C_2$-$C_6$-alkenyl radical, in particular vinyl or allyl, or an alkynyl radical, preferably ethynyl.

$R^1$ and $R^2$ can also each be an acyl radical, preferably a $C_2$-$C_6$-acyl radical, in particular an acetyl radical.

Examples of suitable organosilicon compounds of the formula (I) are $SiCl_4$, $MeSiCl_3$, $Me_2SiCl_2$ and $Me_3SiCl$.

Suitable organosilicon compounds of the formula (IV) are, for example, $Si(OEt)_4$, $MeSi(OEt)_3$, $Me_2Si(OEt)_2$ and $Me_3SiOEt$.

Suitable compounds of the formula (V) are, for example, $Me_3Si(NMeCOMe)$ and $MeSi(NMeCOCH_2C_6H_5)$.

An example of a suitable compound of the formula (VI) is $(MeO)_3SiNMe_2$.

Examples of suitable oligomeric and polymeric organosilicon compounds are methylsilicones and ethylsilicones.

Very particularly preferred organosilicon binders are methylsilicones, for example the Silres® products from Wacker.

In a first step of the process of the present invention, zirconium dioxide powder is mixed with the organosilicon binder, if desired a pore former, if desired an acid, water and, if desired, further additives to give a kneadable composition. Preference is given to mixing a) from 50 to 98% by weight of zirconium dioxide powder,
b) from 2 to 50% by weight, particularly preferably from 5 to 20% by weight, of the organosilicon compound,
c) from 0 to 48% by weight, particularly preferably from 0 to 10% by weight, of pore formers, and
d) from 0 to 48% by weight, particularly preferably from 0 to 10% by weight, of further additives, where the sum of the components a) to d) is 100% by weight, with addition of water and an acid to give a kneadable composition.

The zirconium dioxide powder is zirconium dioxide powder having a high surface area, usually an essentially monoclinic zirconium dioxide powder. Essentially monoclinic zirconium dioxide powder comprising from 85 to 100% by weight, preferably from 90 to 100% by weight, of monoclinic zirconium dioxide can, as described in EP-A 0 716 883, be prepared by precipitation of zirconium salts with ammonia. This is achieved by adding a zirconyl nitrate or zirconyl chloride solution to an aqueous ammonia solution, resulting in the pH dropping from 14 to 6, and washing, drying and calcining the precipitated product. For this purpose, a highly concentrated, generally from 2 to 5 mol %, zirconium chloride solution is firstly prepared from zirconium carbonate and hydrochloric acid or a highly concentrated, generally from 2 to 5 mol %, zirconium nitrate solution is prepared from zirconium carbonate and nitric acid. This solution is generally added to an aqueous ammonia solution (about 15 mol % of $NH_3$) at from 20 to 60° C. while monitoring the pH; the addition is stopped at a pH of 6-8 and the pH must not drop below 6. This is followed by further stirring for a time of generally from 30 to 600 minutes.

The precipitated product is, for example, washed on a filter press and substantially freed of ammonia salts, dried and calcined in air at from 300 to 600° C., preferably from 400 to 500° C. and a pressure of from 0.05 to 1 bar. The essentially monoclinic zirconium dioxide prepared in this way occasionally still contains small amounts of the tetragonal or cubic modification. The proportion of the tetragonal or cubic modification can be reduced to the X-ray crystallographic detection limit by drying the product at a partial pressure of water vapor of from 0.2 to 0.9 bar before calcination. This drying takes, for example, about 16 hours at 120° C.

Water is usually added to the zirconium dioxide powder and the organosilicon compound in order to obtain a kneadable composition.

Furthermore, an acid can be added to the catalyst support composition. This serves to peptize the kneadable composition. Examples of suitable acids are nitric acid and acetic acid; preference is given to nitric acid.

The catalyst support composition usually further comprises a pore former. Suitable pore formers are, for example, polyalkylene oxides such as polyethylene oxide, carbohydrates such as cellulose and sugar, natural fibers, pulp or synthetic polymers such as polyvinyl alcohol.

The catalyst support composition can further comprise additional additives. Examples of additional additives are known compounds which influence the rheology.

The components a) to f) are mixed and homogenized in customary mixing apparatuses. Suitable apparatuses are, for example, kneaders, edge runner mills, Mix-Mullers which ensure good mixing and homogenization of the initially inhomogeneous kneadable composition. The catalyst support composition is subsequently shaped to produce shaped bodies, for example by extrusion to form rods or hollow supports.

The shaped catalyst bodies are then usually dried. Drying is carried out, for example, at from 90 to 120° C. for a period of from 10 to 100 hours.

The dried shaped catalyst support body is subsequently calcined. Calcination is usually carried out at from 300 to 800° C., preferably from 400 to 600° C., for a period of from 0.5 to 6 hours. Calcination is preferably carried out in air and at atmospheric pressure.

The catalyst supports of the present invention are suitable for producing hydrogenation and dehydrogenation catalysts as are described, for example, in DE-A 196 54 391. These comprise, on the catalyst support, one or more elements selected from the group consisting of the elements of transition groups VIII and VI, if desired together with one or more further elements selected from the group consisting of the elements of main groups I and II, transition group III including the lanthanides, main group III, rhenium, zinc and tin.

Particularly useful dehydrogenation-active elements are metals of transition group VIII, preferably the noble metals platinum and palladium, particularly preferably platinum.

If a noble metal is used as dehydrogenation-active element, it is possible for additional metals which slow the sintering of the noble metal, e.g. Re and/or Sn, to be present.

Possible further elements are ones which are known to be able to influence the acidity of the catalyst surface or stabilize the noble metals against sintering. Such further elements are elements of main groups I and II, namely Li, Na, K, Rb, Cs, Mg, Ca, Sr and Ba and also elements of transition group III including the lanthanides, in particular Y and La. Zn has also been found to be effective.

In place of a noble metal, it is also possible for dehydrogenation-active metals of transition group VI, in particular chromium or molybdenum, to be present on the catalyst support.

The dehydrogenation-active metal(s) are generally applied by impregnation with suitable compounds of the metals concerned. Suitable compounds are those which can be converted into the corresponding metal oxide by calcination. The metal compound(s) can also be sprayed on. Suitable metal salts are, for example, the nitrates, acetates and chlorides of the metals, and complex anions of the metals are also possible. Preference is given to using $H_2PtCl_6$ or $Pt(NO_3)_2$ for applying platinum and $Cr(NO_3)_3$ or $(NH_4)_2CrO_4$ for applying chromium. To apply alkali metals and alkaline earth metals, use is advantageously made of aqueous solutions of compounds which can be converted into the corresponding oxides by calcination. Suitable compounds are, for example, hydroxides, carbonates, oxalates, acetates or basic carbonates of the alkali metals and alkaline earth metals. If the catalyst support is doped with metals of main or transition group III, use is frequently made of the hydroxides, carbonates, nitrates, acetates, formates or oxalates which can be converted into the corresponding oxides by calcination, for example $La(OH)_3$, $La_3(CO_3)_2$, $La(NO_3)_3$, lanthanum acetate, lanthanum formate or lanthanum oxalate.

The calcination of the catalyst supports of the present invention impregnated with the metal salt solution concerned is usually carried out at from 350 to 650° C. for a period of from 0.5 to 6 hours.

The present invention also provides the catalysts obtainable using the catalyst supports of the present invention. These are preferably used as hydrogenation catalysts or dehydrogenation catalysts.

Particular preference is given to using the catalysts of the present invention for the dehydrogenation of propane to propene.

The invention is illustrated by the following examples.

EXAMPLES

Preparation of the Catalyst Supports

Example 1

200 g of $ZrO_2$ powder which has been heat-treated beforehand at 450° C. for 3 hours are kneaded together with 41.7 g of 3-methacryloxypropyltrimethoxysilane (silane MEMO from Sivento), 6 g of Zusoplast PS1 (from Zschimmer & Schwarz), 6 ml of 65% strength by weight $HNO_3$ and 92 ml of water for 30 minutes. The doughy composition obtained is shaped in a ram extruder to give extrudates having an external diameter of 3 mm. The extrudates are dried at 120° C. and subsequently calcined at 560° C. for 4 hours. The support obtained has a BET surface area of 109 $m^2/g$ and a porosity of 0.48 ml/g (measured by mercury porosimetry) and has a bimodal pore diameter distribution with maxima at 20 and 1100 nm. The cutting hardness of the support is 25 N.

Example 2

3680 g of $ZrO_2$ powder which has been heat-treated beforehand at 450° C. for 3 hours are mixed with 262.6 g of methoxysilane (Silres MSE 100 from Wacker), 110.4 g of polyethylene oxide (Alkox E100), 110.4 g of 65% strength by weight $HNO_3$ and 1270 g of water for 20 minutes in an edge runner mill. The resulting doughy composition is shaped in a screw extruder to give extrudates having an external diameter of 3 mm. The extrudates are dried at 120° C. and subsequently heat-treated at 560° C. for 4 hours. The support obtained has a BET surface area of 95 $m^2/g$ and a porosity of 0.36 ml/g (measured by mercury porosimetry) and has a bimodal pore diameter distribution with maxima at 20 and 450 nm. The cutting hardness of the support is 35 N.

Example 3

200 g of $ZrO_2$ powder which has been heat-treated beforehand at 450° C. for 3 hours are kneaded together with 6 g of polyethylene oxide (Alkox E100), 10.1 g of Aerosil 200 (from Degussa), 6 ml of 65% strength by weight $HNO_3$ and 100 ml of water for 30 minutes. The doughy composition obtained is shaped in a ram extruder to give extrudates having an external diameter of 3 mm. The extrudates are dried at 120° C. and subsequently calcined at 560° C. for 4 hours. The support obtained has a BET surface area of 75 $m^2/g$, a porosity measured by means of Hg porosimetry of 0.49 ml/g and a cutting hardness of 22 N.

Preparation of the Catalyst Precursors

Example 4

The support material prepared as described in Example 3 is crushed and a sieve fraction of 1.6-2 mm is obtained. The crushed support is coated with the active components Pt/Sn/K/Cs and La by the method described below.

0.1814 g of $H_2PtCl_6.6H_2O$ and 0.2758 g of $SnCl_2.2H_2O$ are dissolved in 138 ml of ethanol and added to 23 g of the $ZrO_2/SiO_2$ support material from Example 3 in a rotary evaporator. The supernatant ethanol is taken off on the rotary evaporator in a water pump vacuum (20 mbar) at a water bath temperature of 40° C. The solid is subsequently dried at 100° C. for 15 hours and then calcined at 560° C. for 3 hours, in each case in stationary air. A solution of 0.1773 g of $CsNO_3$, 0.3127 g of $KNO_3$ and 2.2626 g of $La(NO_3)_3.6H_2O$ in 55 ml of $H_2O$ is then poured over the dried solid. The supernatant water is taken off on a rotary evaporator in a water pump vacuum (20 mbar) at a water bath temperature of 85° C. The solid is subsequently dried at 100° C. for 15 hours and then calcined at 560° C. for 3 hours, in each case under stationary air. The catalyst precursor obtained in this way will hereinafter be referred to as catalyst precursor 1.

Example 5

The support material prepared as described in Example 2 is crushed and a sieve fraction of 1.6-2 mm is obtained. The crushed support is coated with the active components Pt/Sn/K/Cs and La by the method described below.

0.2839 g of $H_2PtCl_6.6H_2O$ and 0.4317 g of $SnCl_2.2H_2O$ are dissolved in 216 ml of ethanol and added to 36 g of the $ZrO_2/SiO_2$ support material from Example 2 in a rotary evaporator. The supernatant ethanol is taken off on the rotary evaporator in a water pump vacuum (20 mbar) at a water bath temperature of 40° C. The solid is subsequently dried at 100° C. for 15 hours and then calcined at 560° C. for 3 hours, in each case in stationary air. A solution of 0.2784 g of $CsNO_3$, 0.4894 g of $KNO_3$ and 3.5399 g of $La(NO_3)_3.6H_2O$ in 86 ml of $H_2O$ is then poured over the dried solid. The supernatant water is taken off on a rotary evaporator in a water pump vacuum (20 mbar) at a water bath temperature of 85° C. The solid is subsequently dried at 100° C. for 15 hours and then calcined at 560° C. for 3 hours, in each case under stationary air. The catalyst precursor obtained in this way will hereinafter be referred to as catalyst precursor 2.

Catalyst Activation

The activation of the catalysts prepared in Examples 4 and 5 for the dehydrogenation of propane is carried out in a laboratory reactor under the following conditions:

An upright tube reactor is charged in each case with 20 ml of catalyst precursor 1 or 2 (reactor length: 520 mm; wall thickness 2 mm; internal diameter: 20 mm; reactor material: internally alonized, i.e. aluminum oxide-coated steel tube; heating: electric (furnace of BASF in-house construction) over a length of 450 mm in the middle of the length of the tube; length of the catalyst bed: 60 mm; position of the catalyst bed: in the middle of the length of the tube reactor; filling of the remaining reactor volume at the top and bottom with steatite spheres (inert material) having a diameter of 4-5 mm, resting on a support at the bottom).

9.3 standard l/h of hydrogen are subsequently passed through the reaction tube for 30 minutes with the external wall temperature along the heating zone being regulated to 500° C. (based on a tube through which an identical inert gas stream is passed). The hydrogen stream is subsequently replaced at the same wall temperature firstly by a stream of 23.6 standard l/h of a mixture of 80% by volume of nitrogen and 20% by volume of air for 30 minutes and then by an identical stream of pure air for 30 minutes. While maintaining the wall temperature, the tube is then flushed with an identical stream of $N_2$ for 15 minutes and the catalyst is finally reduced with 9.3 standard l/h of hydrogen for 30 minutes. The activation of the catalyst precursor is thus concluded.

Dehydrogenation of Crude Propane

Catalytic testing of the activated catalyst precursors 1 and 2 prepared in Examples 4 and 5 was in each case carried out subsequent to the activation of the catalyst in the same reactor using a mixture of 20 standard l/h of crude propane, 18 g/h of water vapor and 1 standard l/h of nitrogen. Crude propane was metered in by means of a mass flow regulator from Brooks, while the water was initially introduced in liquid form by means of an HPLC pump (from Bischoff) into the vaporizer, vaporized in this and then mixed with the crude propane and nitrogen. The gas mixture was subsequently passed over the catalyst. The wall temperature was 622° C.

The pressure at the outlet of the reactor was set to 1.5 bar absolute by means of a pressure regulator (from REKO) located at the reactor outlet.

The product gas which had been depressurized to atmospheric pressure downstream of the pressure regulator was cooled, resulting in the water vapor present in it condensing out. The remaining uncondensed gas was analyzed by means of GC (HP 6890 with Chem-Station, detectors: FID, WLD, separation columns: $Al_2O_3$/KCl (Chrompack), Carboxen 1010 (Supelco)). The reaction gas was also analyzed in an analogous fashion.

The tables below show the results achieved as a function of the operating time. The figures reported are in percent by volume based on "dry" gas, i.e. the amount of water vapor present was in all cases disregarded.

TABLE 1

Activated catalyst precursor 1 from Example 4 (comparison)

| | Reaction gas % by volume | Product gas (after 1 h) % by volume | Product gas (after 9 h) % by volume |
|---|---|---|---|
| Propane | 96.408 | 39.198 | 42.764 |
| Propene | 0.014 | 24.598 | 23.741 |
| $H_2$ | 0 | 30.942 | 29.281 |
| $N_2$ | 3.5 | 2.648 | 2.875 |
| Ethane | 0.078 | 0.544 | 0.450 |
| Ethene | 0 | 0.234 | 0.258 |
| $CH_4$ | 0 | 0.836 | 0.631 |

TABLE 2

Activated catalyst precursor 2 from Example 5 (according to the present invention)

| | Reaction gas % by volume | Product gas (after 1 h) % by volume | Product gas (after 9 h) % by volume |
|---|---|---|---|
| Propane | 96.408 | 28.924 | 31.934 |
| Propene | 0.014 | 26.574 | 27.953 |
| $H_2$ | 0 | 38.530 | 36.011 |
| $N_2$ | 3.5 | 2.386 | 2.490 |
| Ethane | 0.078 | 1.159 | 0.734 |
| Ethene | 0 | 1.166 | 0.677 |
| $CH_4$ | 0 | 0.261 | 0.201 |

As can be seen from the tables, the catalyst according to the present invention has a significantly higher activity than the comparative catalyst.

We claim:

1. A catalyst comprising one or more elements selected from the group consisting of the elements of transition metal groups VIII and VI and optionally one or more further elements selected from the group consisting of the elements of main groups I and II, transition metal group III including the lanthanides, main group III, rhenium, zinc and tin on a catalyst support, wherein said catalyst support is prepared by mixing zirconium dioxide powder with a monomeric, oligomeric or polymeric organosilicon compound as a binder, optionally a pore former, optionally an acid, water and optionally further additives to form a kneadable composition, homogenizing the composition, shaping the composition to produce shaped bodies, drying and calcining.

2. A catalyst as claimed in claim 1, wherein the binder is a monomeric, oligomeric or polymeric silane, alkoxysilane, aryloxysilane, acyloxysilane, oximinosilane, halosilane, aminoxysilane, aminosilane, amidosilane, silazane or silicone.

3. A catalyst as claimed in claim 2, wherein the binder is selected from among the compounds of the formulae (I) to (VII)

$$(Hal)_xSiR_{4-x} \tag{I}$$

$$(Hal)_xSi(OR^1)_{4-x} \tag{II}$$

$$(Hal)_xSi(NR^1R^2)_{4-x} \tag{III}$$

$$R_xSi(OR^1)_{4-x} \tag{IV}$$

$$R_xSi(NR^1R^2)_{4-x} \tag{V}$$

$$(R^1O)_xSi(NR^1R^2)_{4-x} \tag{VI}$$

where

Hal are each, independently of one another, halogen (F, Cl, Br or I),

R are each, independently of one another, H or a substituted or unsubstituted alkyl, alkenyl, alkynyl, cycloalkyl, cycloalkenyl, arylalkyl or aryl radical, $R^1$, $R^2$ are each, independently of one another, H or a substituted or unsubstituted alkyl, acyl, arylalkyl or aryl radical, and x is from 0 to 4.

4. A catalyst as claimed in claim 1, wherein
   a) from 50 to 98% by weight of zirconium dioxide powder,
   b) from 2 to 50% by weight of the organosilicon compound as binder,
   c) from 0 to 48% by weight of pore formers, and
   d) from 0 to 48 by weight of further additives,
   where the sum of the components a) to d) is 100% by weight,
   are mixed with addition of water and an acid to form a kneadable composition.

5. A catalyst as claimed in claim 1, wherein the zirconium dioxide powder consists essentially of monoclinic zirconium dioxide powder.

6. A method of dehydrogenating propane to propene which comprises contacting propane with the catalyst of claim 1.

* * * * *